(12) United States Patent
Kang et al.

(10) Patent No.: US 12,708,524 B2
(45) Date of Patent: Aug. 18, 2026

(54) HEIGHT-ADJUSTABLE SPINAL FUSION CAGE

(71) Applicant: L&K BIOMED CO., LTD., Yongin-si (KR)

(72) Inventors: Gook Jin Kang, Seoul (KR); Jong Hoon Moon, Busan (KR)

(73) Assignee: L&K BIOMED CO., LTD., Yongin-si (KR)

( * ) Notice: Subject to any disclaimer, the term of this patent is extended or adjusted under 35 U.S.C. 154(b) by 287 days.

(21) Appl. No.: 18/289,791

(22) PCT Filed: Sep. 14, 2022

(86) PCT No.: PCT/KR2022/013731
§ 371 (c)(1),
(2) Date: Nov. 7, 2023

(87) PCT Pub. No.: WO2024/053770
PCT Pub. Date: Mar. 14, 2024

(65) Prior Publication Data

US 2025/0090344 A1 Mar. 20, 2025

(30) Foreign Application Priority Data

Sep. 5, 2022 (KR) ........................ 10-2022-0111927

(51) Int. Cl.
*A61F 2/44* (2006.01)
*A61F 2/30* (2006.01)

(52) U.S. Cl.
CPC .... *A61F 2/447* (2013.01); *A61F 2002/30199* (2013.01); *A61F 2002/30537* (2013.01)

(58) Field of Classification Search
CPC .................... A61F 2/447; A61F 2/4455; A61F 2002/30199; A61F 2002/30537;
(Continued)

(56) References Cited

U.S. PATENT DOCUMENTS 7,731,751 B2 6/2010 Butler et al.
8,398,713 B2 * 3/2013 Weiman .................... A61F 2/44 623/17.11
(Continued)

FOREIGN PATENT DOCUMENTS

KR 10-2106024 B1 4/2020
KR 10-2195237 B1 12/2020
(Continued)

OTHER PUBLICATIONS

L&K Biomed Co., Ltd., Grace Period Inventor-Originated Disclosure—35 USC 102(b)(1)(A), Positing on Internet, Mar. 14, 2022. Mar. 15, Jun. 2, 2022. Jul. 25, 2022., Aug. 3, 2022. Aug. 10, 2022., pp. 15.
(Continued)

*Primary Examiner* — Jessica Weiss
(74) *Attorney, Agent, or Firm* — Sughrue Mion, PLLC

(57) ABSTRACT

A height-adjustable spinal fusion cage including a first end plate and a second end plate, a distal movement block fixed to be relatively movable to a dove-tail groove formed at a distal end of each of the first end plate and the second end plate, a proximal movement block fixed to be relatively movable to a dove-tail groove formed at a proximal end of each of the first end plate and the second end plate, an adjusting member rotatably fixed to the proximal movement block and screw-coupled to the distal movement block to adjust a distance between the distal movement block and the proximal movement block, and a vertical guide portion formed to be disposed at the first end plate and the second end plate and provide support for a load in a longitudinal direction or width direction of the first end plate and the second end plate.

7 Claims, 9 Drawing Sheets

(58) Field of Classification Search
CPC .. A61F 2002/30331; A61F 2002/30387; A61F 2002/30405; A61F 2002/30492; A61F 2002/30507
USPC ............................................ 623/17.15–17.16
See application file for complete search history.

(56) References Cited

U.S. PATENT DOCUMENTS 8,512,407 B2 8/2013 Butler et al.
8,894,712 B2 * 11/2014 Varela .................... A61F 2/447 623/17.16
8,940,048 B2 1/2015 Butler et al.
9,034,041 B2 5/2015 Wolters et al.
9,801,733 B2 10/2017 Wolters et al.
10,154,911 B2 12/2018 Predick et al.
10,172,718 B2 1/2019 Wolters et al.
10,383,741 B2 8/2019 Butler et al.
10,426,632 B2 10/2019 Butler et al.
10,682,239 B2 6/2020 Hsu et al.
11,033,403 B2 6/2021 Predick et al.
11,103,362 B2 8/2021 Butler et al.
11,446,156 B2 9/2022 Hunziker et al.
11,464,649 B2 10/2022 Kang et al.
2006/0224241 A1 10/2006 Butler et al.
2008/0140207 A1 * 6/2008 Olmos .................. A61F 2/4455 623/17.11
2010/0305705 A1 12/2010 Butler et al.
2013/0123924 A1 5/2013 Butler et al.
2013/0197647 A1 8/2013 Wolters et al.
2013/0211526 A1 8/2013 Alheidt et al.
2014/0257484 A1 * 9/2014 Flower .................. A61F 2/4455 29/460
2015/0374507 A1 * 12/2015 Wolters ............. A61B 17/8858 623/17.15
2017/0224504 A1 8/2017 Butler et al.
2017/0224505 A1 * 8/2017 Butler ....................... A61F 2/44
2017/0367842 A1 12/2017 Predick et al.
2018/0133024 A1 5/2018 Wolters et al.
2018/0193160 A1 * 7/2018 Hsu ......................... A61F 2/447
2018/0193164 A1 7/2018 Shoshtaev
2018/0296361 A1 * 10/2018 Butler ................... A61F 2/4455
2019/0290448 A1 9/2019 Predick et al.
2019/0307577 A1 10/2019 Predick et al.
2019/0374348 A1 12/2019 Butler et al.
2020/0129307 A1 * 4/2020 Hunziker ................ A61F 2/447
2020/0383798 A1 12/2020 Butler et al.
2021/0106434 A1 * 4/2021 Alheidt ................... A61F 2/442
2021/0128315 A1 5/2021 Predick
2021/0259448 A1 8/2021 Morgan
2021/0259848 A1 8/2021 Kang et al.
2021/0259852 A1 8/2021 Predick et al.
2021/0353427 A1 11/2021 Butler et al.
2022/0409392 A1 12/2022 Kim et al.
2022/0409395 A1 12/2022 Hunziker et al.
2023/0046487 A1 * 2/2023 Kang ...................... A61F 2/447
2023/0172725 A1 6/2023 Kang et al.

FOREIGN PATENT DOCUMENTS

KR 10-2195238 B1 12/2020
WO 2021/187712 A1 9/2021

OTHER PUBLICATIONS

International Search Report for PCT/KR2022/013731 dated May 31, 2023.

Extended European search report (EESR) issued on Jul. 30, 2024 for related European Patent Application No. 22937678.5.

* cited by examiner

HEIGHT-ADJUSTABLE SPINAL FUSION CAGE

CROSS REFERENCE TO RELATED APPLICATIONS

This application is a National Stage of International Application No. PCT/KR2022/013731 filed Sep. 14, 2022, claiming priority based on Korean Patent Application No. 10-2022-0111927 filed Sep. 5, 2022, the entire disclosures of which are incorporated herein by reference.

TECHNICAL FIELD

The present disclosure relates to a height-adjustable spinal fusion cage, and more particularly, to a spinal fusion cage which is inserted between vertebral bodies at the lowest height and is height-adjustable while inserted.

BACKGROUND ART

The vertebral body is a portion that is made up of 32 to 35 vertebrae and intervertebral disks positioned between the vertebrae and connects the skull positioned above the vertebral body and the pelvis positioned under the vertebral body to constitute the center of the human body.

The vertebrae include, from above, seven cervical vertebrae, twelve thoracic vertebrae, five lumbar vertebrae, five sacral vertebrae, and three to five coccygeal vertebrae, and in adults, the five sacral vertebrae constitute one sacrum, and the three to five coccygeal vertebrae constitute one coccyx.

Spinal fusion is one treatment method that has been used for a long period of time to treat serious spinal diseases. Spinal fusion is a surgical method in which an intervertebral disk is removed, and a cage replacing the intervertebral disk is inserted to fuse adjacent vertebrae to each other.

When performed on lumbar vertebrae, spinal fusion may be classified into Posterior Lumbar Interbody Fusion (PLIF), Transformational Lumbar Interbody Fusion (TLIF), Lateral Lumbar Interbody Fusion (LLIF), Oblique Lumbar Interbody Fusion (OLIF), Anterior Lumbar Interbody Fusion (ALIF), and the like according to a direction of the insertion of the cage.

PLIF is a method in which an incision is made along the center line of the spine so that the vertebral body is entirely exposed, a portion of the posterior side of the spinal bone is removed, an intervertebral disk is removed, and then a PLIF cage is inserted.

PLIF is the type of spinal fusion that has been performed for the longest time and is an essential method when performing two-level or three-level interbody fusion. However, due to the surgical process, there is a high possibility of adhesion to nerves, ligaments, and muscles, the healing time is long due to a large incision area, and there are significant side effects in some people.

As the PLIF cage, a pair of small cages are placed on both left and right sides. The PLIF cage is the smallest among cages used in all types of spinal fusion.

TLIF is a surgical method in which a small incision is made along both sides of the spinal muscles, the vertebral body is exposed to a minimum, and then, while a spinal joint area is removed in a direction in which a neural foramen is formed, a TLIF cage is inserted into an intervertebral disk. This surgical technique has advantages of reducing bleeding and shortening the surgery time and thus is suitable for one-level interbody fusion. However, when multilevel interbody fusion is necessary, PLIF surgery should be performed. Most TLIF cages have an arc shape, and thus, the TLIF cage is placed in the vertebral body and rotated so that a convex part of the TLIF cage is ventrally facing. The TLIF cage is larger than the PLIF cage, but a support area of the TLIF cage is smaller than a LLIF cage or ALIF cage which will be mentioned below.

ALIF has various advantages such as quick recovery after surgery and no concern about adhesion but has a disadvantage of requiring highly skilled techniques due to being performed by making an incision in the front (ventral side) and approaching the spine past the internal organs. The ALIF cage has an advantage of having the largest support area among the cages used in all types of spinal fusion.

LLIF has been developed to overcome the disadvantages of ALIF, PLIF, and TLIF. Due to being performed through a side incision, LLIF has advantages that, not only is it possible to further widen the space in a narrowed area between vertebrae compared to existing back incision surgeries, damage to surrounding tissues hardly occurs. However, since the psoas muscle and peritoneum are present around the surgical path, there is a problem such as thigh muscle paralysis when a mistake is made during surgery. The LLIF cage is smaller than the ALIF cage but is larger than the PLIF cage or TLIF cage.

A safer and more effective surgical method compared to LLIF is OLIF or Anterior To Psoas (ATP) fusion. OLIF is performed with a surgical path in a direction oblique from a side and has an advantage of being possible even between the fourth lumbar vertebra (L4) and the fifth lumbar vertebra (L5), where surgery is difficult by DLIF, due to the psoas muscle and peritoneum. Also, the possibility of damaging the nerves, which is a problem in LLIF, is significantly less.

Existing spinal fusion cages are manufactured as one body with no change in cross-sectional area or height using a metal material such as titanium or a polymer material such as polyetheretherketone (PEEK). Therefore, the existing spinal fusion cages have a fairly large number of product configurations that take into account the patient's physique, height, race, gender, and the like. That is, there has been a burden on the manufacturer's part to produce dozens to hundreds of product lines by combining the three variables, width, length, and height.

Also, gaps between vertebrae of patients do not increase at regular intervals, and when spinal fusion cages are mass-produced, surgery should be performed by selecting a spinal fusion cage with an appropriate height from already-existing product lines, which causes a problem of not being able to properly correspond to each patient.

Various attempts have been made to address the above, and a height-adjustable spinal fusion cage has been developed.

U.S. Unexamined Patent Application Publication No. 2017-0224505 discloses a height-adjustable assembly. Specifically, the assembly includes first and second support bodies configured to come in contact with adjacent vertebrae, a first wedge member fixed to be relatively movable to a plate inclined portion formed at one end of each of the first and second support bodies, a second wedge member fixed to be relatively movable to a plate inclined portion formed at the other end of each of the first and second support bodies, an adjusting member rotatably fixed to the second wedge member and screw-coupled to the first wedge member to adjust a distance between the first wedge member and the second wedge member, a columnar U-shaped concave portion formed at the first support body toward the second support body, and a columnar aligning member formed at the second support body toward the first support body and configured to constrain a direction of movement in which the first and second support bodies approach each other or move away from each other by sliding with the U-shaped concave portion.

However, in the assembly, since the columnar aligning member is coupled to the U-shaped concave portion, only a portion of an outer surface of the aligning member is surrounded by the U-shaped concave portion. Thus, there is a problem that the aligning member may be detached from the concave portion in the case in which the assembly is inserted into the vertebral body and a load strongly acts on the assembly in the width direction and longitudinal direction.

Patent Document

U.S. Unexamined Patent Application Publication No. 2017-0224505 (Date of Publication: Aug. 10, 2017)

DISCLOSURE

Technical Problem

The present disclosure is directed to providing a spinal fusion cage which is height-adjustable while inserted and stably supports movement of a pair of end plates.

Technical Solution

One aspect of the present disclosure provides a height-adjustable spinal fusion cage including a first end plate and a second end plate configured to come in contact with adjacent vertebrae, a distal movement block fixed to be relatively movable to a dove-tail groove formed at a distal end of each of the first end plate and the second end plate, a proximal movement block fixed to be relatively movable to a dove-tail groove formed at a proximal end of each of the first end plate and the second end plate, an adjusting member rotatably fixed to the proximal movement block and screw-coupled to the distal movement block to adjust a distance between the distal movement block and the proximal movement block, and a vertical guide portion formed to be disposed at the first end plate and the second end plate and provide support for a load in a longitudinal direction or width direction of the first end plate and the second end plate, wherein the vertical guide portion includes a pair of first vertical guides configured to vertically extend from the first end plate toward the second end plate and have a transverse cross-section extending in one direction and a pair of second vertical guides configured to have a slot groove into which the first vertical guide is inserted formed therein and constrain a direction of movement in which the first end plate and the second end plate approach each other or move away from each other by sliding with the first vertical guides.

In one embodiment, the first end plate and the second end plate may include a central portion and a pair of extensions connected to both sides of the central portion and extending in a distal direction and a proximal direction.

In one embodiment, the first end plate and the second end plate may be formed in an H-shape in which a distal end and a proximal end are open.

In one embodiment, the slot groove of the second vertical guide may be formed to surround an entire outer surface of the first vertical guide.

In one embodiment, the first vertical guide may include a first arc portion, a second arc portion spaced a predetermined distance apart from the first arc portion, and a pair of horizontal portions connecting the first arc portion and the second arc portion.

In one embodiment, the second vertical guide may include a first arc wall, a second arc wall spaced a predetermined distance apart from the first arc wall, and a pair of horizontal walls connecting the first arc wall and the second arc wall, and the slot groove which penetrates in a vertical direction may be formed by the first arc wall, the second arc wall, and the pair of horizontal walls.

In one embodiment, the first arc portion may come in contact with an inner side surface of the first arc wall, the second arc portion may come in contact with an inner side surface of the second arc wall, and the pair of horizontal portions may come in contact with inner side surfaces of the pair of horizontal walls.

In one embodiment, the first vertical guide may include a concave groove recessed in a thickness direction.

In one embodiment, a marking groove may be disposed at inner surfaces of the first and second end plates that face each other.

In one embodiment, a dove-tail configured to be coupled to the dove-tail groove and slide may be formed at an upper portion and a lower portion of each of the distal movement block and the proximal movement block.

In one embodiment, an inclined groove configured to induce insertion of the first vertical guide may be formed around the slot groove.

Advantageous Effects

According to one aspect of the present disclosure, since a first vertical guide has a transverse cross-section that longitudinally extends in one direction, and a second vertical guide is formed of a slot groove structure that corresponds to the first vertical guide, the overall mechanical strength of a spinal fusion cage can be excellent.

The advantageous effects of the present disclosure are not limited to that described above and should be understood as including all effects inferable from the detailed description of the present disclosure or configurations of the disclosure described in the claims.

DESCRIPTION OF DRAWINGS

FIG. 14 shows a half-sectional view and a partially enlarged view of the spinal fusion cage of FIG. 1.

MODES OF THE INVENTION

Figure 1:
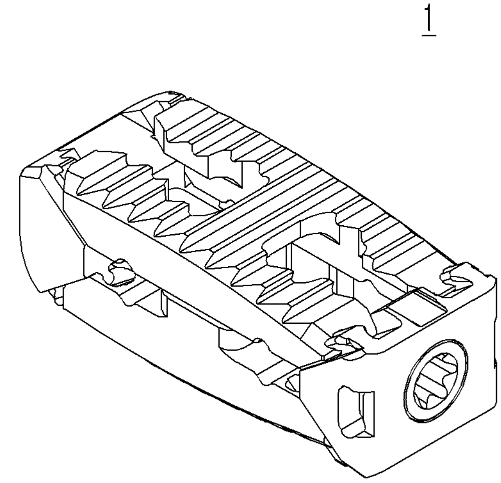
FIG. 1 is a perspective view of a lowest-height state of a spinal fusion cage according to the present disclosure.

Hereinafter, the present disclosure will be described with reference to the accompanying drawings. However, the present disclosure may be implemented in various different forms and thus is not limited to the embodiments described herein. Also, in the drawings, parts irrelevant to the description have been omitted to clearly describe the present disclosure, and like parts are denoted by like reference numerals throughout the specification.

Throughout the specification, when a certain part is described as being "connected" to another part, this includes not only the case in which the certain part is "directly connected" to the other part, but also the case in which the certain part is "indirectly connected" to the other part with another member disposed therebetween. Also, when a certain part is described as "including" a certain element, the certain part may further include another element instead of excluding other elements unless particularly described otherwise.

Terms including ordinals such as "first" or "second" used herein may be used to describe various elements or operations, but the corresponding elements or operations should not be limited by the ordinals. The terms including ordinals should be construed as only distinguishing one element or operation from other elements or operations.

Hereinafter, embodiments of the present disclosure will be described in detail with reference to the accompanying drawings.

Figure 2:
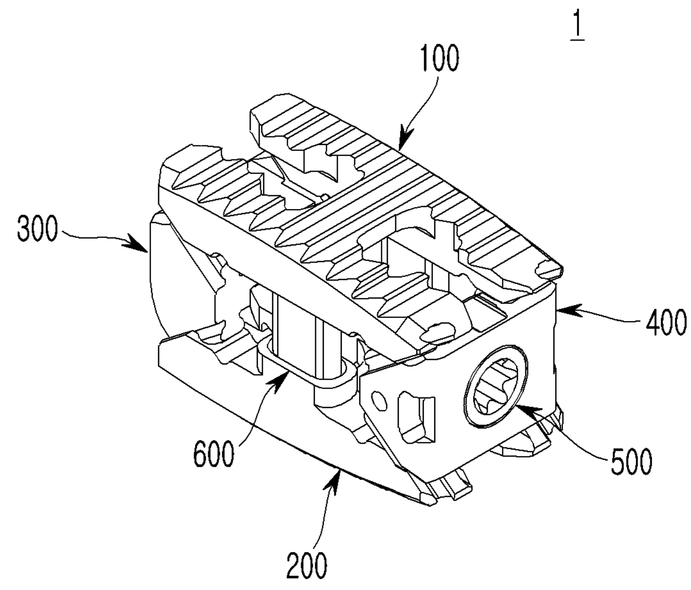
FIG. 2 is a perspective view of a highest-height state of the spinal fusion cage of FIG. 1.
Figure 3:
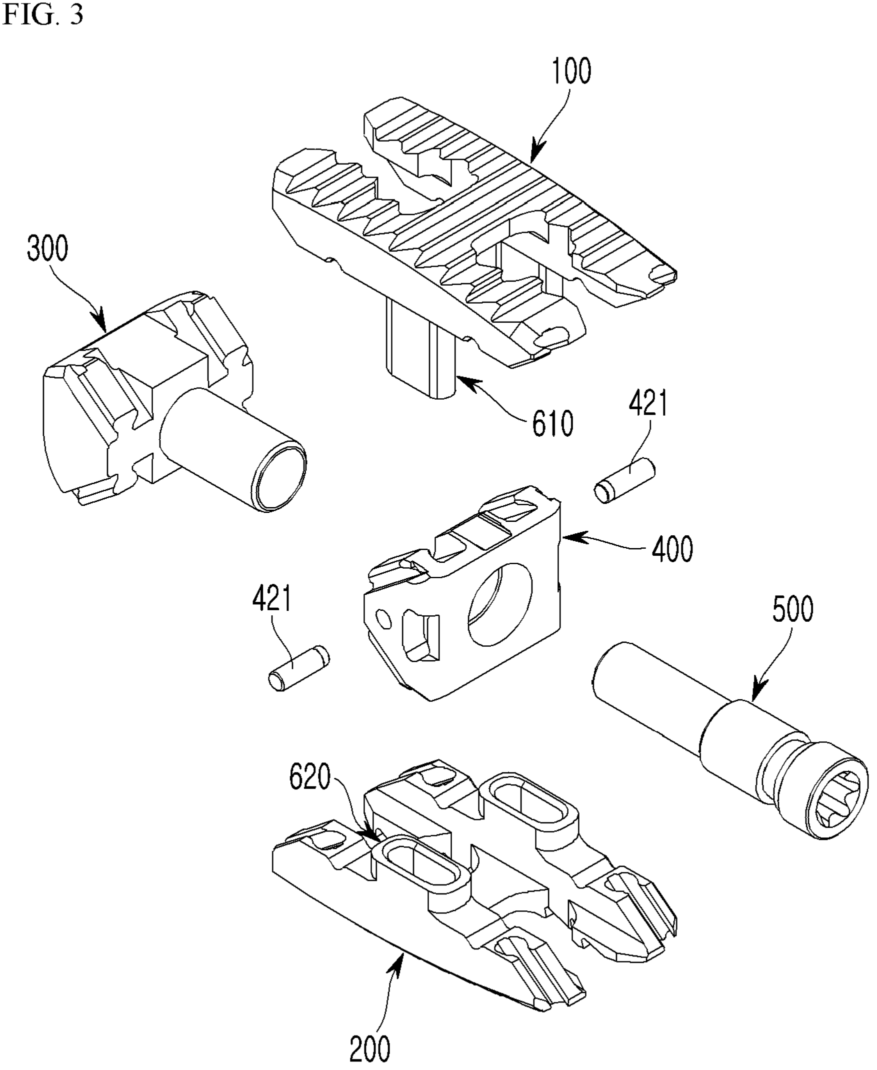
FIG. 3 is an exploded perspective view of the spinal fusion cage of FIG. 1 viewed from the top.

FIG. 1 is a perspective view of a lowest-height state of a spinal fusion cage according to the present disclosure, FIG. 2 is a perspective view of a highest-height state of the spinal fusion cage of FIG. 1, and FIG. 3 is an exploded perspective view of the spinal fusion cage of FIG. 1 viewed from the top.

As illustrated in FIGS. 1 to 3, a spinal fusion cage 1 according to one embodiment of the present disclosure mainly includes a first end plate 100 and a second end plate 200 disposed to vertically face each other, a distal movement block 300 and a proximal movement block 400 disposed between the first end plate 100 and the second end plate 200 to move according to a distance between the first end plate 100 and the second end plate 200, an adjusting member 500 connected to the distal movement block 300 by passing through the proximal movement block 400, and a vertical guide portion 600 formed to be disposed at the first end plate 100 and the second end plate 200 and provide support for a load in the longitudinal direction or width direction of the first end plate 100 and the second end plate 200.

Figure 4:
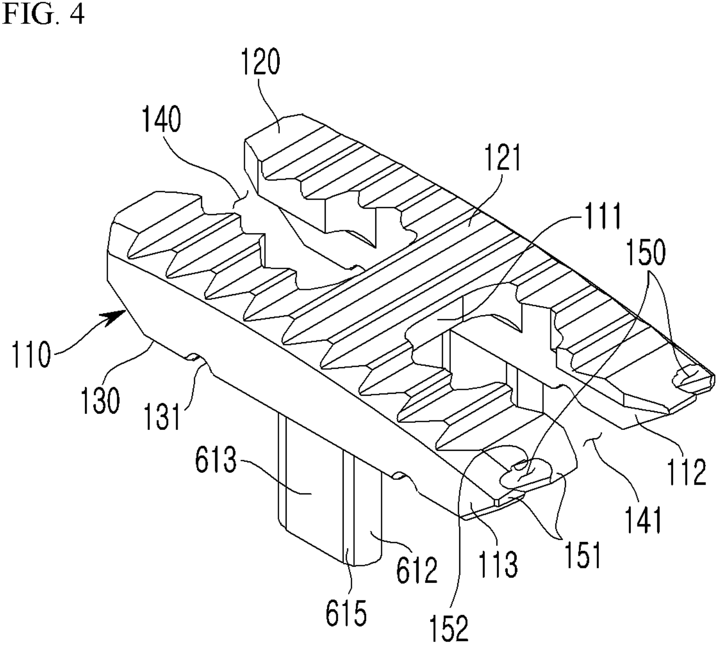
FIG. 4 is a perspective view of a first end plate of the spinal fusion cage of FIG. 1 viewed from the top.
Figure 5:
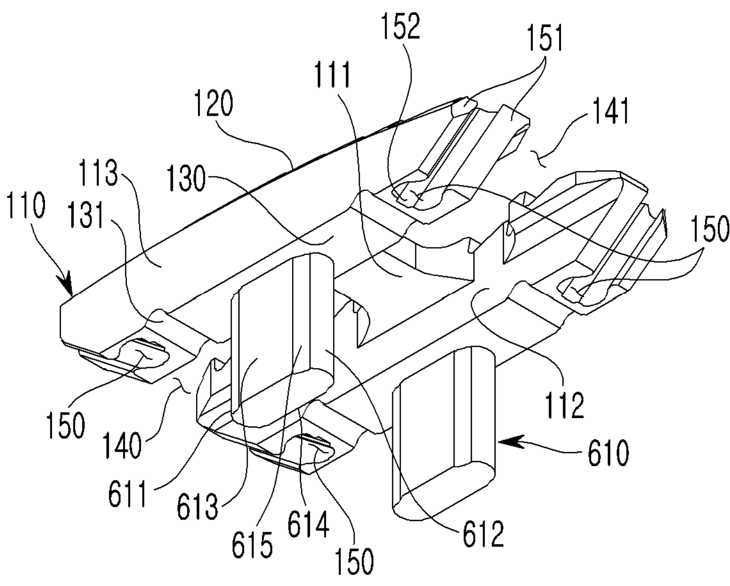
FIG. 5 is a perspective view of the first end plate of the spinal fusion cage of FIG. 1 viewed from the bottom.

FIG. 4 is a perspective view of the first end plate of the spinal fusion cage of FIG. 1 viewed from the top, and FIG. 5 is a perspective view of the first end plate of the spinal fusion cage of FIG. 1 viewed from the bottom.

As illustrated in FIGS. 4 and 5, the first end plate 100 has a first end plate body 110 coming in contact with the vertebral body. Specifically, the first end plate body 110 is configured to include a central portion 111 and a pair of extensions 112 and 113 formed at both ends of the central portion 111 to be perpendicular to the central portion 111 and to extend in both side directions.

The extensions 112 and 113 may be formed to be spaced a predetermined distance apart in the width direction by the central portion 111, the first end plate body 110 may have a substantially H-shape, and openings 140 and 141 are formed at both ends of the first end plate body 110 in the longitudinal direction.

A bone graft material is inserted into the spinal fusion cage 1 while the spinal fusion cage 1 is expanded. In the present disclosure, by forming the openings 140 and 141, there is an effect of increasing the space into which the bone graft material can be inserted. With an increase in the bone graft material insertion space in this way, when the spinal fusion cage 1 is inserted into the human body, a contact area with bone is widened, which has an effect of achieving excellent bone fusion.

A tooth-shaped protrusion 121 may be formed on an outer surface 120 of the first end plate body 110 to prevent detachment from the vertebral body.

Also, a first dove-tail groove 150 is formed at both longitudinal side ends of the extensions 112 and 113 of the first end plate body 110. That is, a total of four first dove-tail grooves 150 may be formed on the first end plate body 110. A first dove-tail 330 of the distal movement block 300 and a third dove-tail 430 of the proximal movement block 400 may be accommodated in the first dove-tail grooves 150. A pair of first guide rails 151 are disposed to face each other at both sides of the first dove-tail groove 150. The pair of first guide rails 151 are spaced apart in the width direction of the extensions 112 and 113 and are formed so that a separation distance therebetween gradually decreases toward ends of the extensions 112 and 113. The first guide rails 151 formed in a distal direction or proximal direction of the extensions 112 and 113 are both formed to be inclined in a direction gradually approaching the center of the first end plate body 110 from the outer surface 120 of the first end plate body 110 toward an inner surface 130 thereof.

Preferably, a friction reduction groove 152 recessed at a predetermined depth toward the central portion 111 may be formed at the center of the first dove-tail groove 150. The left-right width of the friction reduction groove 152 is formed to be smaller than the left-right width of the first and third dove-tails 330 and 430, and the friction reduction groove 152 does not come in contact with outer surfaces of the first and third dove-tails 330 and 430. That is, the friction reduction groove 152 of the first end plate 100 may reduce a frictional force generated during sliding of the distal movement block 300 or the proximal movement block 400 and easily move the distal movement block 300 or the proximal movement block 400.

Also, a marking groove 131 is disposed on inner surfaces 130 of the first end plate 100 that face each other. Specifically, the marking groove 131 is formed to be recessed at a predetermined depth in the thickness direction of the first end plate 100 along the width direction of the extensions 112 and 113 of the first end plate 100. For example, the marking groove 131 may be formed in a semi-cylindrical shape substantially in a width direction. The marking groove 131 serves to facilitate identification of the spinal fusion cage 1 during radiography after the spinal fusion cage 1 is inserted into the vertebral body.

Figure 6:
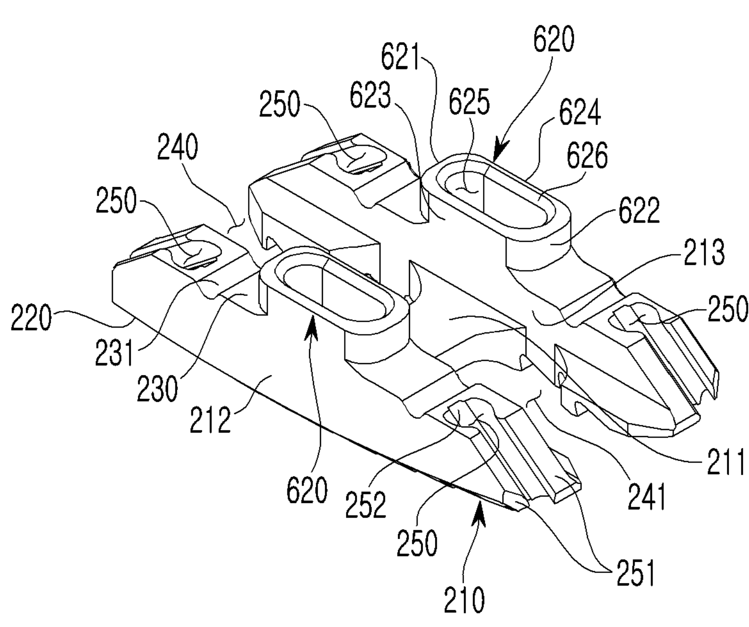
FIG. 6 is a perspective view of a second end plate of the spinal fusion cage of FIG. 1 viewed from the top.
Figure 7:
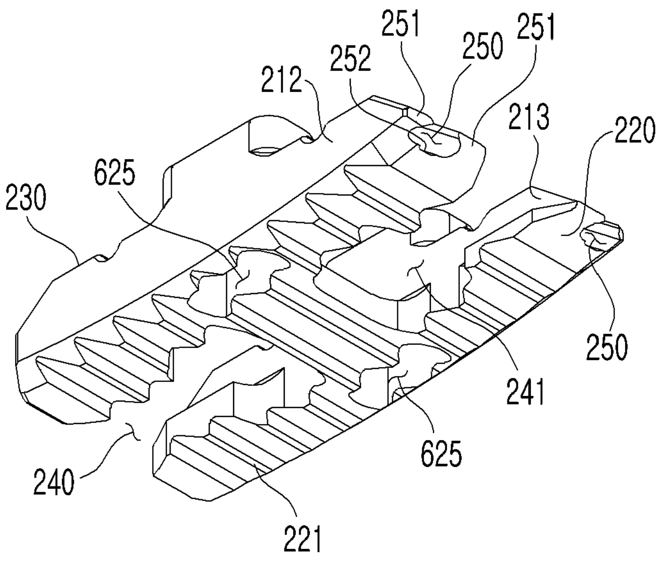
FIG. 7 is a perspective view of the second end plate of the spinal fusion cage of FIG. 1 viewed from the bottom.

FIG. 6 is a perspective view of the second end plate of the spinal fusion cage of FIG. 1 viewed from the top, and FIG. 7 is a perspective view of the second end plate of the spinal fusion cage of FIG. 1 viewed from the bottom.

As illustrated in FIGS. 6 and 7, the second end plate 200 has a second end plate body 210 coming in contact with the vertebral body. Specifically, the second end plate body 210 is configured to include a central portion 211 and extensions 212 and 213 formed at both ends of the central portion 211 to be perpendicular to the central portion 211 and to extend in both side directions.

The extensions 212 and 213 may be formed to be spaced a predetermined distance apart in the width direction by the central portion 211, the second end plate body 210 may have a substantially H-shape, and openings 240 and 241 are formed at both ends of the second end plate body 210 in the longitudinal direction.

As in the above description, a bone graft material is inserted into the spinal fusion cage 1 while the spinal fusion cage 1 is expanded. In the present disclosure, by forming the openings 240 and 241, there is an effect of increasing the space into which the bone graft material can be inserted. With an increase in the bone graft material insertion space in this way, when the spinal fusion cage 1 is inserted into the human body, a contact area with bone is widened, which has an effect of achieving excellent bone fusion.

A tooth-shaped protrusion 221 may be formed on an outer surface 220 of the second end plate body 210 to prevent detachment from the vertebral body.

Also, a second dove-tail groove 250 is formed at both longitudinal side ends of the extensions 212 and 213 of the second end plate body 210. That is, a total of four second dove-tail grooves 250 may be formed on the second end plate body 210. A second dove-tail 340 of the distal movement block 300 and a fourth dove-tail 440 of the proximal movement block 400 may be accommodated in the second dove-tail grooves 250. A pair of second guide rails 251 are disposed to face each other at both sides of the second dove-tail groove 250. The pair of second guide rails 251 are spaced apart in the width direction of the extensions 212 and 213 and are formed so that a separation distance therebetween gradually decreases toward ends of the extensions 212 and 213. The second guide rails 251 formed in a distal direction and proximal direction of the extensions 212 and 213 are both formed to be inclined in a direction gradually approaching the center of the second end plate body 210 from the outer surface 220 of the second end plate body 210 toward an inner surface 230 thereof.

Preferably, a friction reduction groove 252 recessed at a predetermined depth toward the central portion 211 may be formed at the center of the second dove-tail groove 250. The left-right width of the friction reduction groove 252 is formed to be smaller than the left-right width of the second and fourth dove-tails 340 and 440, and the friction reduction groove 252 does not come in contact with outer surfaces of the second and fourth dove-tails 340 and 440. That is, the friction reduction groove 252 of the second end plate 200 may reduce a frictional force generated during sliding of the distal movement block 300 or the proximal movement block 400 and easily move the distal movement block 300 or the proximal movement block 400.

Also, a marking groove 231 is disposed on inner surfaces 230 of the second end plate 200 that face each other. Specifically, the marking groove 231 is formed to be recessed at a predetermined depth in the thickness direction of the second end plate 200 along the width direction of the extensions 212 and 213 of the second end plate 200. For example, the marking groove 231 may be formed in a semi-cylindrical shape substantially in a width direction. The marking groove 231 serves to facilitate identification of the spinal fusion cage 1 during radiography after the spinal fusion cage 1 is inserted into the vertebral body.

Since the spinal fusion cage 1 is inserted into the human body, there are great limitations on the size and shape of the spinal fusion cage 1. Still, the spinal fusion cage 1 should have an angle for implementing a basic degree of curvature of the spine (an angle in the longitudinal direction of the spine, that is, a direction of a sagittal plane, based on a transverse plane). Since the size of the adjusting member 500 should have an outer diameter for withstanding a load despite a height limit, an end portion of the first end plate 100 or the second end plate 200 to which the distal movement block 300 or the proximal movement block 400 is coupled becomes thin, which acts as a weakness when a load is imparted, and in particular, such a phenomenon becomes more prominent with an increase in the angle. In the present disclosure, in order to address the above, as illustrated in FIGS. 4 to 7, the openings 140 and 240 are disposed at the upper and lower sides of the distal movement block 300, and the openings 141 and 241 are disposed at the upper and lower sides of the proximal movement block 400 to remove the thin portion in advance.

Figure 8:
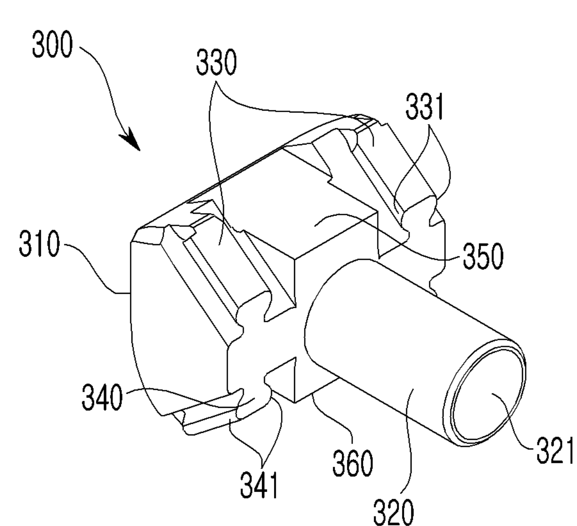
FIG. 8 is a perspective view of a distal movement block of the spinal fusion cage of FIG. 1 viewed from the upper front side.
Figure 9:
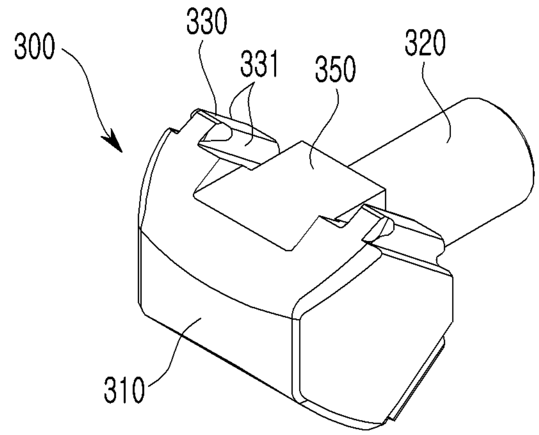
FIG. 9 is a perspective view of the distal movement block of the spinal fusion cage of FIG. 1 viewed from the upper rear side.
Figure 10:
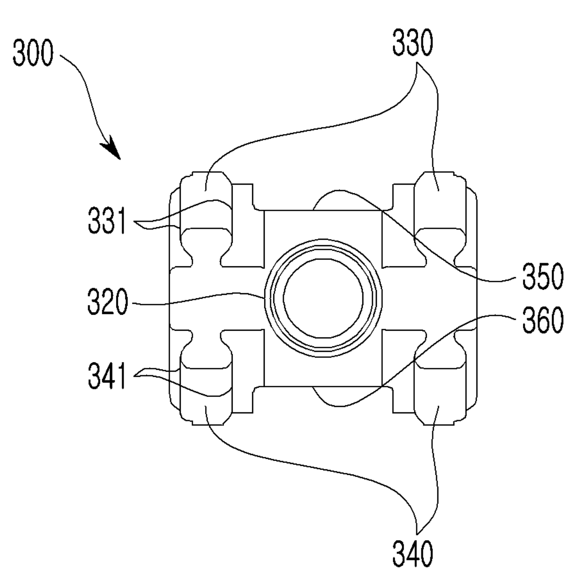
FIG. 10 is a front view of the distal movement block of the spinal fusion cage of FIG. 1.

FIG. 8 is a perspective view of the distal movement block of the spinal fusion cage of FIG. 1 viewed from the upper front side, FIG. 9 is a perspective view of the distal movement block of the spinal fusion cage of FIG. 1 viewed from the upper rear side, and FIG. 10 is a front view of the distal movement block of the spinal fusion cage of FIG. 1.

As illustrated in FIGS. 8 to 10, the distal movement block 300 has an insertion portion 310 formed in a streamlined shape by protruding in a distal direction so that it is easy to insert the distal movement block 300 between vertebrae. Also, a connecting portion 320 is longitudinally formed in a proximal direction at the central portion of the distal movement block 300, and a connecting screw portion 321 having screw threads is formed inside the connecting portion 320. Also, a pair of first dove-tails 330 corresponding to the first dove-tail grooves 150 of the first end plate 100 are formed at both sides of an upper portion of the distal movement block 300, and a pair of second dove-tails 340 corresponding to the second dove-tail grooves 250 of the second end plate 200 are formed at both sides of a lower portion of the distal movement block 300.

First protrusions 331 corresponding to the first guide rails 151 are formed around the first dove-tails 330. When the first dove-tails 330 are accommodated in the first dove-tail grooves 150, the first guide rails 151 and the first protrusions 331 are coupled to each other and slide, and the distal movement block 300 is prevented from being detached from the first end plate 100. Second protrusions 341 corresponding to the second guide rails 251 are formed around the second dove-tails 340. When the second dove-tails 340 are accommodated in the second dove-tail grooves 250, the second guide rails 251 and the second protrusions 341 are coupled to each other and slide, and the distal movement block 300 is prevented from being detached from the second end plate 200.

A first support surface 350 which is formed to be parallel to the inner surface 130 of the first end plate body 110 and comes in surface contact with the inner surface 130 of the first end plate body 110 is formed at the center of the upper portion of the distal movement block 300. A second support surface 360 which is formed to be parallel to the inner surface 230 of the second end plate body 210 and comes in surface contact with the inner surface 230 of the second end plate body 210 is formed at the center of the lower portion of the distal movement block 300. While the height of the spinal fusion cage 1 is the lowest, since a portion of the inner surface 130 of the first end plate body 110 comes in surface contact with the first support surface 350, and a portion of the inner surface 230 of the second end plate body 210 comes in surface contact with the second support surface 360, the first end plate 100 and the second end plate 200 are restricted from approaching each other.

Figure 11:
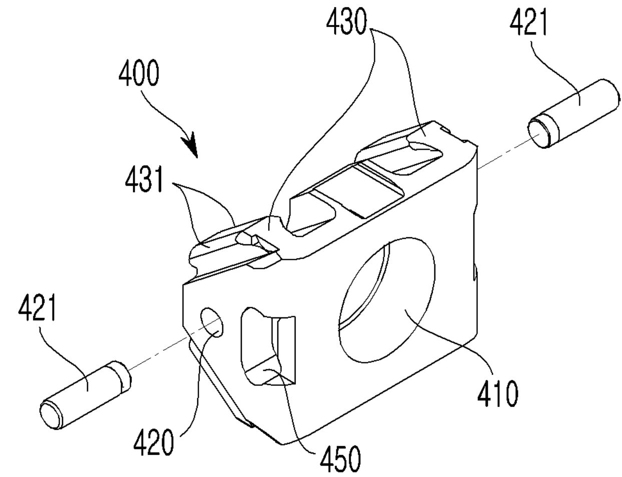
FIG. 11 is a perspective view of a proximal movement block of the spinal fusion cage of FIG. 1 viewed from the upper front side.
Figure 12:
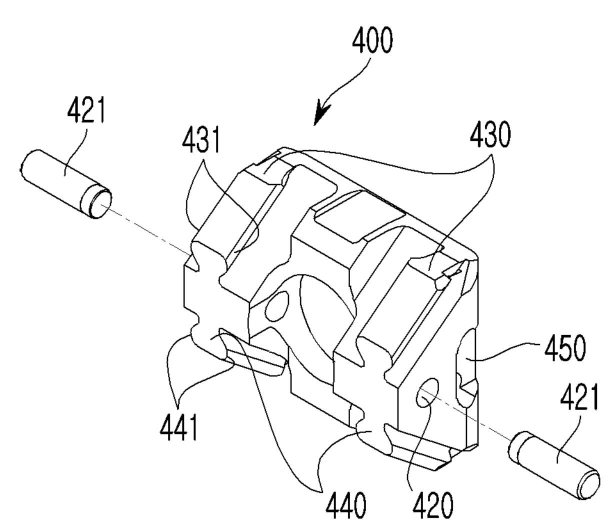
FIG. 12 is a perspective view of the proximal movement block of the spinal fusion cage of FIG. 1 viewed from the upper rear side.

FIG. 11 is a perspective view of the proximal movement block of the spinal fusion cage of FIG. 1 viewed from the upper front side, and FIG. 12 is a perspective view of the proximal movement block of the spinal fusion cage of FIG. 1 viewed from the upper rear side.

As illustrated in FIGS. 11 and 12, the proximal movement block 400 has an adjusting member hole 410 formed therein to rotatably support the adjusting member 500. Also, a pair of third dove-tails 430 corresponding to the first dove-tail grooves 150 of the first end plate 100 are formed at both side ends of an upper portion of the proximal movement block 400, and a pair of fourth dove-tails 440 corresponding to the second dove-tail grooves 250 of the second end plate 200 are formed at both side ends of a lower portion of the proximal movement block 400.

Third protrusions 431 corresponding to the first guide rails 151 are formed around the third dove-tails 430. As the third dove-tails 430 are accommodated in the first dove-tail grooves 150, the first guide rails 151 and the third protrusions 431 are coupled to each other, and the proximal movement block 400 is prevented from being detached from the first end plate 100. Fourth protrusions 441 corresponding to the second guide rails 251 are formed around the fourth dove-tails 440. As the fourth dove-tails 440 are accommodated in the second dove-tail grooves 250, the second guide rails 251 and the fourth protrusions 441 are coupled to each other, and the proximal movement block 400 is prevented from being detached from the second end plate 200.

That is, since the first and second end plates 100 and 200 according to one embodiment of the present disclosure have a total of eight dove-tail grooves 150 and 250 provided on longitudinal ends thereof, and the eight dove-tails 330, 340, 430, and 440 formed on the distal movement block 300 and the proximal movement block 400 are coupled to the dove-tail grooves 150 and 250, stress can be more effectively distributed even when the spinal fusion cage 1 is inserted into the vertebral body and receives a load in the width direction and longitudinal direction of the spinal fusion cage 1 in addition to the height direction of the spinal fusion cage 1 according to movement of the human body.

Also, a pin hole 420 in which a pin member 421 is accommodated is formed at a side portion of the proximal movement block 400. Also, a fastening portion 450 is formed at the side portion of the proximal movement block 400 for the spinal fusion cage 1 to be gripped by a tool.

The distal movement block 300 and the proximal movement block 400 have a substantially wedge-like shape and support the first end plate 100 and the second end plate 200 to lift or lower the first end plate 100 and the second end plate 200.

Figure 13:
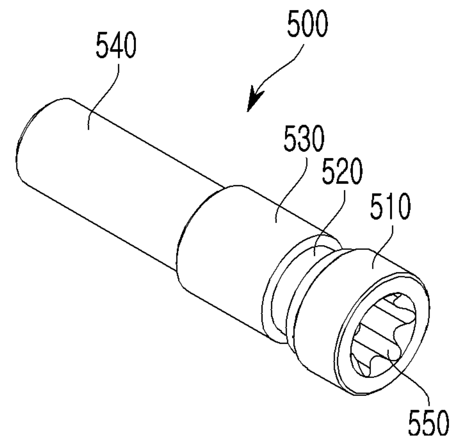
FIG. 13 is a perspective view of an adjusting member of the spinal fusion cage of FIG. 1.
Figure 14:
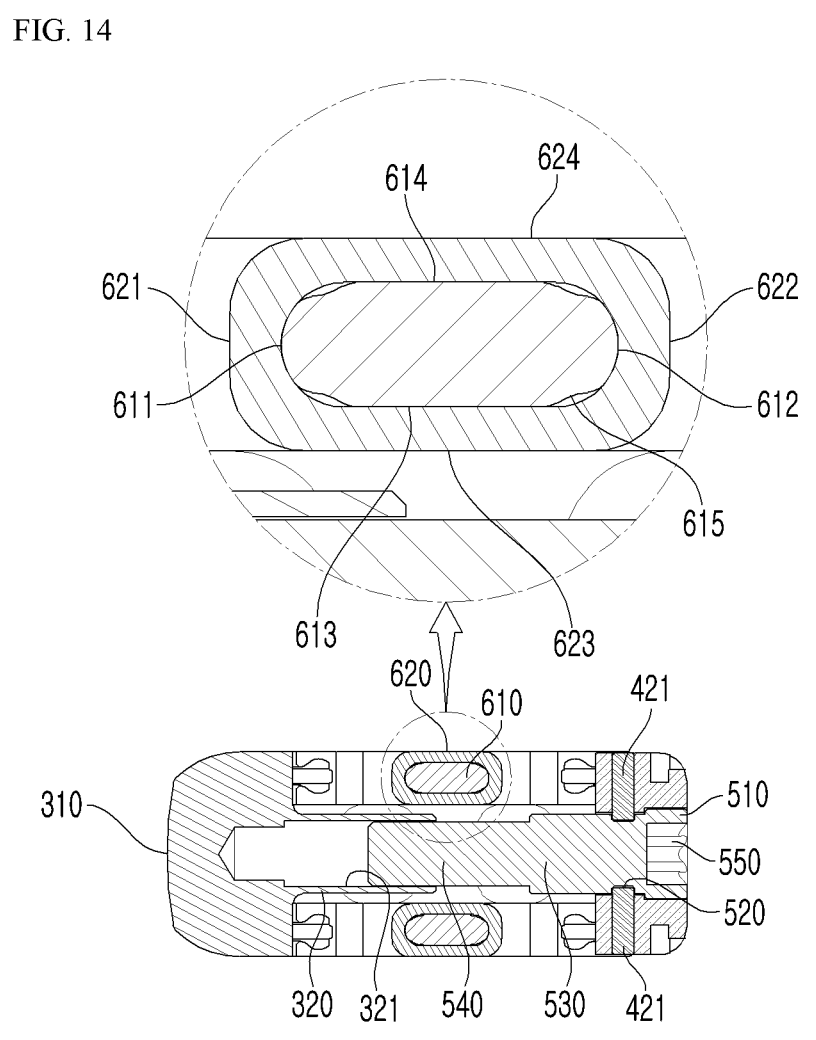

FIG. 13 is a perspective view of the adjusting member of the spinal fusion cage of FIG. 1. As illustrated in FIG. 13, the adjusting member 500 may have a substantially bolt-like shape. That is, the adjusting member 500 has a head 510 and an adjusting screw portion 540. The head 510 is placed in an opening formed in a proximal direction of the adjusting member hole 410, and the adjusting screw portion 540 is screw-coupled to the connecting screw portion 321 of the connecting portion 320 via the adjusting member hole 410. A tool groove 550 that can be connected to a tool s is formed on the head 510. Also, a rotation support portion 530 is positioned between the head 510 and the adjusting member hole 410, and rotation is supported as the rotation support portion 530 comes in contact with an inner wall surface of the adjusting member hole 410. Also, as illustrated in FIG. 14 which will be described below, a pin position portion 520 is formed around the rotation support portion 530, and an end of the pin member 421 inserted through the pin hole 420 of the proximal movement block 400 is placed on the pin position portion 520. As a result, the adjusting member 500 is able to rotate at the correct position.

As illustrated in FIGS. 2 to 7, the vertical guide portion 600 is made of a first vertical guide 610 that extends in the vertical direction from the inner surface 130 of the first end plate 100 and a second vertical guide 620 that extends in the vertical direction from the inner surface 230 of the second end plate 200 and slides with the first vertical guide 610.

The first vertical guide 610 may be formed in a columnar shape that vertically protrudes toward the second end plate 200 from the center of the inner surface 130 of the extensions 112 and 113 of the first end plate 100 and has a cross-section longitudinally extending in one direction. Specifically, an outer surface of the first vertical guide 610 includes a first arc portion 611 disposed at a distal side of the extensions 112 and 113, a second arc portion 612 disposed at a proximal side of the extensions 112 and 113, and a pair of horizontal portions 613 and 614 configured to connect an end of the first arc portion 611 and an end of the second arc portion 612 to each other and formed to be horizontal to the longitudinal direction of the extensions 112 and 113.

The second vertical guide 620 is formed in a columnar shape that vertically protrudes toward the first end plate 100 from the center of the inner surface 230 of the extensions 212 and 213 of the second end plate 200, and a slot groove 625 formed to vertically pass through the outer surface 220 of the second end plate body 210 from an upper portion of the second vertical guide 620 is formed at the center of the second vertical guide 620.

Specifically, the second vertical guide 620 includes a first arc wall 621 disposed at a distal side of the extensions 212 and 213, a second arc wall 622 disposed at a proximal side of the extensions 212 and 213, and a pair of horizontal walls 623 and 624 configured to connect each of an end of the first arc wall 621 and an end of the second arc wall 622. Since the pair of horizontal walls 623 and 624 are disposed to be spaced a predetermined distance apart from each other along the width direction of the extensions 212 and 213, the slot groove 625 into which the first vertical guide 610 may be inserted is formed by the first arc wall 621, the second arc wall 622, and the pair of horizontal walls 623 and 624.

FIG. 14 shows a half-sectional view and a partially enlarged view of the spinal fusion cage of FIG. 1.

As illustrated in FIG. 14, the first arc portion 611 is formed to correspond to an inner side surface of the first arc wall 621, the second arc portion 612 is formed to correspond to an inner side surface of the second arc wall 622, and the pair of horizontal portions 613 and 614 are formed to correspond to inner side surfaces of the pair of horizontal walls 623 and 624.

Therefore, when the first vertical guide 610 is inserted into the second vertical guide 620, the first arc portion 611 is surrounded by the inner side surface of the first arc wall 621, the second arc portion 612 is surrounded by the inner side surface of the second arc wall 622, and the pair of horizontal portions 613 and 614 are surrounded by the inner side surfaces of the pair of horizontal walls 623 and 624. That is, the entire outer surface of the first vertical guide 610 is surrounded by the second vertical guide 620. As a result, the first vertical guide 610 and the second vertical guide 620 are able to stably slide relative to each other.

Preferably, an inclined groove 626 inclined inward is formed around the slot groove 625 which is on the upper portion of the first arc wall 621, the second arc wall 622, and the pair of horizontal walls 623 and 624, and in the case in which the spinal fusion cage 1 is assembled or the height of the spinal fusion cage 1 is increased and then decreased, the first vertical guide 610 is naturally guided to an inner side of the slot groove 625 along the inclined groove 626.

Preferably, a concave groove 615 recessed to be concave in a thickness direction of the first vertical guide 610 may be formed on a boundary between the horizontal portions 613 and 614 and the first arc portion 611 of the first vertical guide 610 and a boundary between the horizontal portions 613 and 614 and the second arc portion 612. When the first vertical guide 610 is inserted into the second vertical guide 620, the concave groove 615 does not come in contact with the inner side surfaces of the first arc wall 621, the second arc wall 622, and the horizontal walls 623 and 624. That is, the concave groove 615 of the first vertical guide 610 reduces a frictional force generated during sliding with the second vertical guide 620 and allows the first vertical guide 610 and the second vertical guide 620 to more smoothly slide relative to each other.

Further, the first vertical guide 610 has a cross-section longitudinally extending in one direction, and the second vertical guide 620 is formed of the structure of the slot groove 625 that corresponds to the first vertical guide 610, and thus force applied in the longitudinal direction of the spinal fusion cage 1 can be better supported. That is, by reducing shear stress acting on the first and second vertical guides 610 and 620, the overall mechanical strength of the spinal fusion cage 1 can be excellent.

Figure 15:
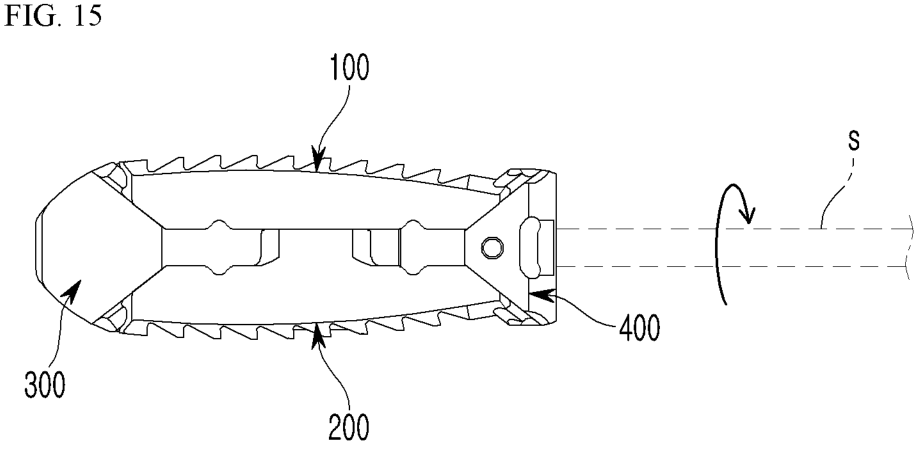
FIG. 15 shows a lateral view of the lowest-height state and a lateral view of the highest-height state of the spinal fusion cage of FIG. 1.
Figure 15:
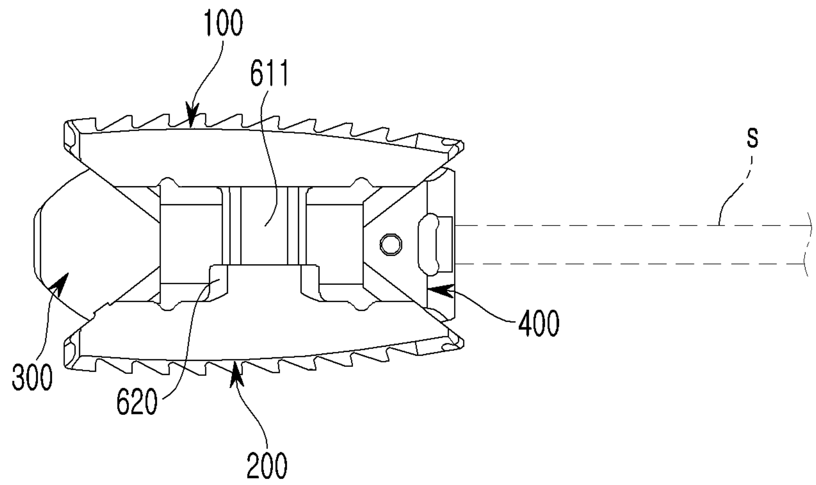

FIG. 15 shows a lateral view of the lowest-height state and a lateral view of the highest-height state of the spinal fusion cage of FIG. 1.

As illustrated in FIG. 15, by inserting the tool s such as a driver into the tool groove and rotating the tool s in one direction, the proximal movement block 400 and the distal movement block 300 may be caused to approach each other, and as a result, movement that causes the first end plate 100 and the second end plate 200 to move away from each other is possible. Likewise, by inserting the tool s and rotating the tool s in the other direction, a distance between the proximal movement block 400 and the distal movement block 300 may be increased, and as a result, movement that causes a distance between the first end plate 100 and the second end plate 200 to decrease is possible.

The above-given description of the present disclosure is only illustrative, and those of ordinary skill in the art to which the present disclosure pertains should understand that the present disclosure can be easily modified to other specific forms without changing the technical spirit or essential features of the present disclosure. Therefore, the embodiments described above should be understood as illustrative, instead of limiting, in all aspects. For example, each element described as a single type may be embodied in a distributed manner, and likewise, elements described as being distributed may be embodied in a combined form.

The scope of the present disclosure is shown by the claims below, and all changes or modifications derived from the meaning and scope of the claims and their equivalent concepts should be construed as falling within the scope of the present disclosure.

DESCRIPTION OF REFERENCE NUMERALS

1: spinal fusion cage
100: first end plate
110: first end plate body
111: central portion
112, 113: extension
120: outer surface
121: tooth-shaped protrusion
130: inner surface
131: marking groove
140, 141: opening
150: first dove-tail groove
151: first guide rail
152: friction reduction groove
200: second end plate
210: second end plate body
211: central portion
212, 213: extension
220: outer surface
221: tooth-shaped protrusion
230: inner surface
231: marking groove
240, 241: opening
250: second dove-tail groove
251: second guide rail
252: friction reduction groove
300: distal movement block
310: insertion portion
320: connecting portion
321: connecting screw portion
330: first dove-tail
331: first protrusion
340: second dove-tail
341: second protrusion
350: first support surface
360: second support surface
400: proximal movement block
410: adjusting member hole
420: pin hole
421: pin member
430: third dove-tail
431: third protrusion
440: fourth dove-tail
441: fourth protrusion
450: fastening portion
500: adjusting member
510: head
520: pin position portion
530: rotation support portion
540: adjusting screw portion
550: tool groove
600: vertical guide portion
610: first vertical guide
611: first arc portion
612: second arc portion
613, 614: horizontal portion
615: concave groove
620: second vertical guide
621: first arc wall
622: second arc wall
623, 624: horizontal wall
625: slot groove
626: inclined groove

The invention claimed is:

1. A height-adjustable spinal fusion cage comprising:

a first end plate and a second end plate configured to come in contact with adjacent vertebrae;

a distal movement block moveably coupled to a dove-tail groove formed at a distal end of each of the first end plate and the second end plate;

a proximal movement block moveably coupled to a dove-tail groove formed at a proximal end of each of the first end plate and the second end plate;

an adjusting member rotatably coupled to the proximal movement block and rotatably-coupled to the distal movement block and configured to adjust a distance between the distal movement block and the proximal movement block;

a first pin member and a second pin member each inserted through a respective pin hole in the proximal movement block and contacting a pin position portion of the adjusting member; and a vertical guide portion configured provide support for a load in a longitudinal direction or width direction along the first end plate and the second end plate, wherein the vertical guide portion includes a pair of first vertical guides vertically extending from the first end plate toward the second end plate and having a transverse cross-section extending in one direction, and a pair of second vertical guides comprising a slot into which a respective one of the first vertical-guides is inserted and limiting a direction of movement in which the first end plate and the second end plate approach each other or move away from each other by sliding with the pair of first vertical guides, wherein each first vertical guide includes a first arc portion, a second arc portion spaced a predetermined distance apart from the first arc portion, and a pair of horizontal portions connecting the first arc portion and the second arc portion, wherein each second vertical guide includes a first arc wall, a second arc wall spaced a predetermined distance apart from the first arc wall, and a pair of horizontal walls connecting the first arc wall and the second arc wall, and each slot extends in a vertical direction and is formed by the first arc wall, the second arc wall, and the pair of horizontal walls, wherein each first arc portion of each first vertical guide comes in contact with an inner side surface of a respective first arc wall of a corresponding second vertical guide, wherein each second arc portion of each first vertical guide comes in contact with an inner side surface of a respective second arc wall of the corresponding second vertical guide, wherein each of the pair of horizontal portions of each first vertical guide comes in contact with inner side surfaces of respective ones of the pair of horizontal walls of the corresponding second vertical guide, and wherein each first vertical guide includes a concave groove extending in a vertical direction and recessed in a thickness direction at a boundary between the horizontal portions and the arc portions.

2. The height-adjustable spinal fusion cage of claim 1, wherein the first end plate and the second end plate each include a central portion and a pair of extensions connected to opposing sides of the central portion and extending in a distal direction and a proximal direction.

3. The height-adjustable spinal fusion cage of claim 2, wherein the first end plate and the second end plate are each formed in an H-shape in which a portion of a distal end and a portion of a proximal end thereof are open.

4. The height-adjustable spinal fusion cage of claim 1, wherein the slot of each second vertical guide is configured to surround an entire outer surface of a respective one of the first vertical guides.

5. The height-adjustable spinal fusion cage of claim 1, wherein a marking groove is disposed along an inner surface of the first end plate and an inner surface of the second end plate, wherein the inner surfaces face each other.

6. The height-adjustable spinal fusion cage of claim 1, wherein a dove-tail is formed along an upper portion and a lower portion of each of the distal movement block and the proximal movement block, wherein each dove-tail is configured to be slidably coupled to a respective one of the dove-tail grooves of the first end plate and the second end plate.

7. The height-adjustable spinal fusion cage of claim 1, wherein an inclined groove configured to facilitate insertion of each first vertical guide is formed around each slot.

* * * * *